(12) United States Patent
Amos et al.

(10) Patent No.: US 7,445,642 B2
(45) Date of Patent: Nov. 4, 2008

(54) AGENT ELUTING STENT AND CATHETER

(75) Inventors: Ray Amos, Spencer, IN (US); Travis Deal, Freedom, IN (US); James F. Scheurmann, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 597 days.

(21) Appl. No.: 11/085,087

(22) Filed: Mar. 22, 2005

(65) Prior Publication Data

US 2005/0234388 A1 Oct. 20, 2005

Related U.S. Application Data

(60) Provisional application No. 60/555,354, filed on Mar. 23, 2004.

(51) Int. Cl.
*A61F 2/04* (2006.01)

(52) U.S. Cl. ............... 623/23.68; 623/23.67; 604/8

(58) Field of Classification Search ............ 623/1.11, 623/23.67–23.68; 604/8
See application file for complete search history.

(56) References Cited

U.S. PATENT DOCUMENTS

| 4,553,959 | A | 11/1985 | Hickey et al. |
| 4,932,938 | A | 6/1990 | Goldberg et al. |
| 5,019,102 | A | 5/1991 | Hoene |
| 5,141,502 | A | 8/1992 | Macaluso, Jr. |
| 5,380,270 | A | 1/1995 | Ahmadzadeh |
| 5,441,515 | A | 8/1995 | Khosravi et al. |
| 5,591,145 | A | 1/1997 | Sachse |
| 5,624,395 | A | 4/1997 | Mikhail et al. |
| 6,102,848 | A | 8/2000 | Porter |
| 6,364,868 | B1 | 4/2002 | Ikeguchi |
| 6,545,097 | B2 | 4/2003 | Pinchuk et al. |
| 6,706,013 | B1 * | 3/2004 | Bhat et al. ............... 604/96.01 |
| 2003/0144624 | A1 * | 7/2003 | Barbut .......................... 604/8 |
| 2003/0195456 | A1 | 10/2003 | Robertson |
| 2004/0193093 | A1 * | 9/2004 | Desmond, III ................. 604/8 |
| 2006/0015190 | A1 * | 1/2006 | Robertson ................ 623/23.67 |

OTHER PUBLICATIONS

International Search Report for International Patent Application No. PCT/US2005/009335, 4 pages.

* cited by examiner

*Primary Examiner*—Suzette J Gherbi
(74) *Attorney, Agent, or Firm*—Cooley Godward Kronish LLP

(57) ABSTRACT

A device for placement within a body of a patient includes an elongated member and an inflatable member coupled to the elongated member. In one embodiment, the elongated member has a first end portion and a second end portion and defines a lumen. The inflatable member is coupled to the elongated member between the first end portion of the elongated member and the second end portion of the elongated member. The inflatable member is configured to be inflated with a fluid and is configured to deliver the fluid to the body of the patient when the device is placed within the body.

29 Claims, 6 Drawing Sheets

AGENT ELUTING STENT AND CATHETER

CROSS-REFERENCES TO OTHER APPLICATIONS

This application claims priority under 35 U.S.C. §119(e) to U.S. Provisional Application No. 60/555,354, filed on Mar. 23, 2004, the entire content of which is hereby incorporated by reference.

BACKGROUND OF THE INVENTION

Non-vascular stents and catheters are commonly used to promote drainage in various parts of the body. For example, ureteral stents are used to create a pathway for urinary drainage from the kidney to the bladder in patients with ureteral obstruction or injury or to protect the integrity of the ureter in a variety of surgical manipulations. Unfortunately, ureteral stents, particularly the portion positioned in the ureter and the bladder, may produce adverse effects including hemorrhage, a continual urge to urinate, flank pain accompanying reflux of urine back up the ureter due to retrograde pressure when voiding, and chronic trigone irritation. Attempts to mitigate some of these problems associated with ureteral stents include administering systemic pharmaceuticals such as antispasmodic drugs. However, it is difficult to deliver such agents to the desired areas of treatment with conventional devices.

The present invention relates to ureteral stents and catheters that elute a fluid containing a therapeutic agent. The invention may be applied to other stents and catheter applications, in other parts of the body, such as urethral stent and biliary stents.

SUMMARY OF THE INVENTION

A device for placement within a body of a patient includes an elongated member and an inflatable member coupled to the elongated member. In one embodiment, the elongated member has a first end portion and a second end portion and defines a lumen. The inflatable member is coupled to the elongated member between the first end portion of the elongated member and the second end portion of the elongated member. The inflatable member is configured to be inflated with a fluid and is configured to deliver the fluid to the body of the patient when the device is placed within the body.

BRIEF DESCRIPTION OF THE DRAWINGS

Like reference characters generally refer to the same parts throughout the different views in the figures.

DETAILED DESCRIPTION

Figure 1:
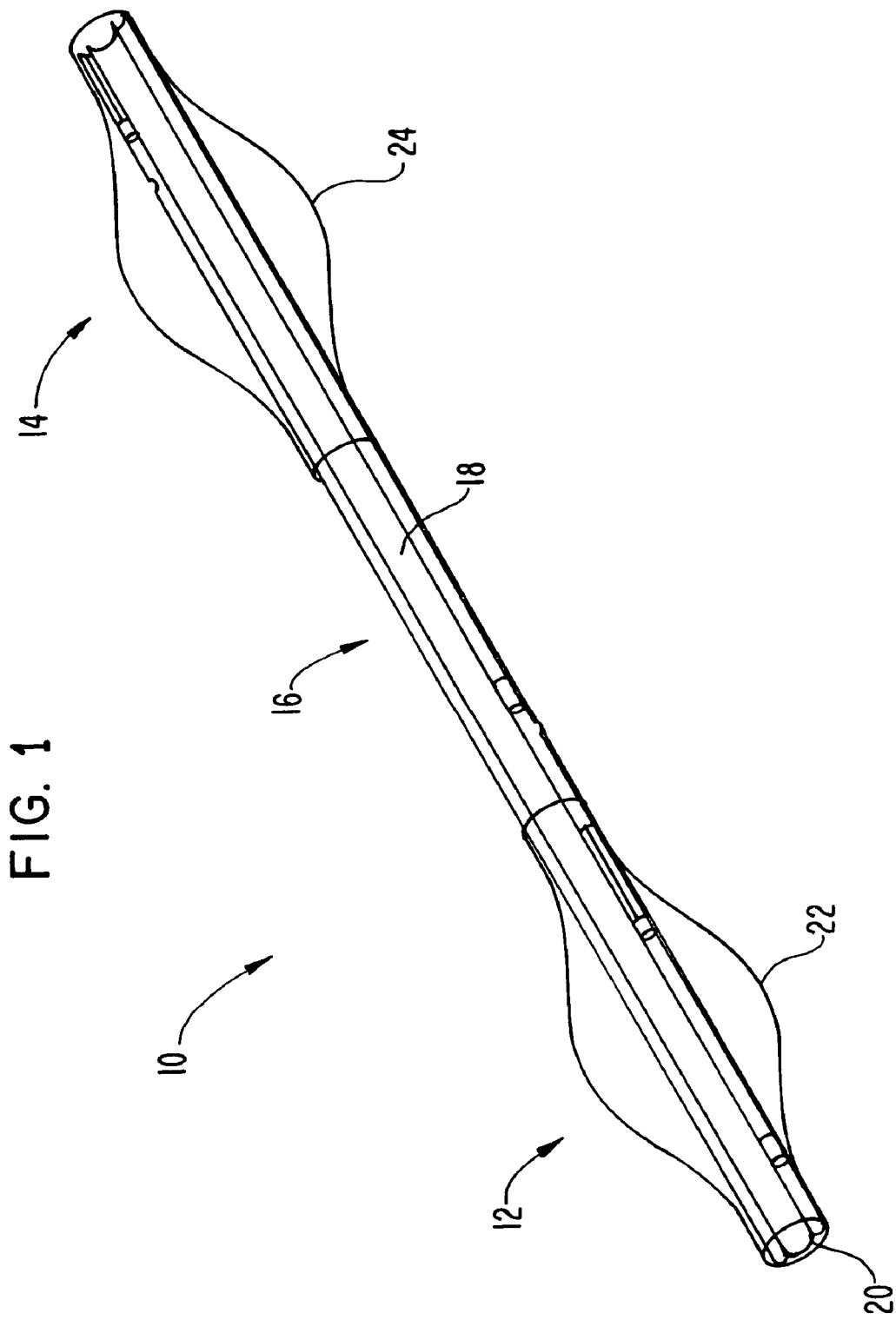
FIG. 1 is a perspective and partial cross-sectional view of a ureteral stent according to one embodiment of the invention.

FIGS. 1-4 illustrate a ureteral stent 10 in accordance with one embodiment of the present invention. The ureteral stent 10 is a drainage device that, when positioned within the ureter of a mammal, assists in reducing fluid retention by facilitating the drainage of urine from the kidney through the ureter and into the urinary bladder. Hence, the ureteral stent 10 is used to create a pathway for urinary drainage from the kidney to the bladder in patients with ureteral obstruction or injury or to protect the integrity of the ureter in a variety of surgical manipulations. The stent 10 may be used to address a number of clinical conditions that can produce interruption in urine flow including, for example, intrinsic obstruction of the ureter due to tumor growth, stricture or stones, compression of the ureter due to extrinsic tumor growth, stone fragment impactation in the ureter following extracorporeal shock wave lithotripsy (ESWL), and ureteral procedures such as ureteroscopy and endopyelotomy. The stent 10 may be used to treat or avoid obstructions of the ureter (such as ureteral stones or ureteral tumors) that disrupt the flow of urine from the corresponding kidney to the urinary bladder. The ureteral stent 10 may also be used after endoscopic inspection of the ureter. The stent 10 may be placed in the ureter to facilitate the flow of urine from the kidney to the bladder and to enable the ureter to heal.

The stent 10 is configured for implantation within the ureter of a patient, and includes a proximal or bladder portion 12, a distal or renal portion 14, and an elongated body portion 16 between the proximal and distal portions. The stent 10 includes a drainage lumen 18 that extends the length of the stent to facilitate the drainage of urine from the kidney through the ureter and into the urinary bladder. The ureteral stent 10 is preferably tubular in shape, terminating in two opposing ends: a kidney distal end and a urinary bladder proximal end. The stent 10 may have one or more drainage holes arranged along the length of the body portion 16 that provide fluid communication between the outside surface of the stent and the drainage lumen 18. A suture loop or other suitable structure may be included on the bladder portion 12 to facilitate removal of the stent 10 from the body after use.

Figure 2:
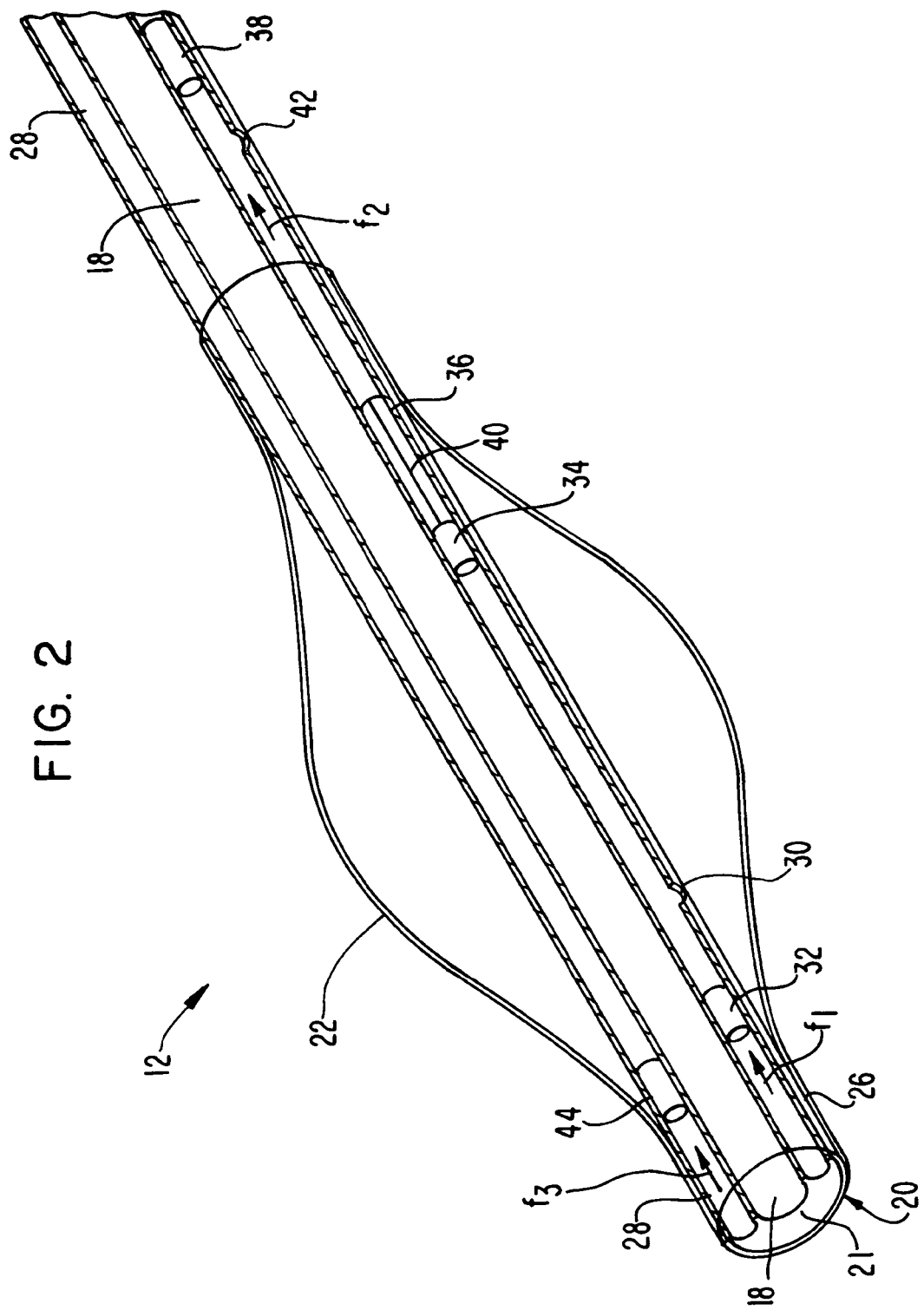
FIG. 2 is an enlarged detail view of the bladder end of the ureteral stent illustrated in FIG. 1.

Typically, in a ureteral application, the length of the elongated body portion 16 ranges between about 18 cm and 30 cm and has an outside diameter of at least about 1.6 mm to 3.3 mm, preferably 2 mm (or French size 6). As is illustrated in FIG. 2, the stent 10 includes a tubular member 20 that extends from the proximal portion 12 to the distal portion 14 and that defines the drainage lumen 18. The thickness of a wall 21 of the tubular member 20 is at least about 0.05 mm to 0.35 mm. The tubular member 20 may be formed from a number of different biocompatible materials. The tubular member 20 may consist of one of these materials or may be formed, for example by extrusion, of two or more materials along its length. One subset of biocompatible best suited for the tubular member 20 exhibit the following characteristics: high tensile strength, high retention coil strength, excellent biocompatibility and biodurability, excellent radiopacity or flouroscopic visibility, availability in varying durometers, and a low resistance to passage. In a preferred embodiment, the tubular member 20 may be constructed from an extruded polymeric tubing, such as PERCUFLEX (Boston Scientific Corporation, Natick, Mass.), C-FLEX (Xomed-Trease, Inc.), FLEXIMA, or other polymer material including polytetrafluoroethylene (PTFE), silicone polyurethane, polyurethane plastics, polyethylene plastics, and thermoplastics, for example. Additional suitable polymers for the tubular member 20 may be selected, for example, from the following:

polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, inlcluding styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above. The tubular member 20 may also include a hydrophilic coating on the outer surface, such as HYDROPLUS coating (Union Carbide).

The proximal or bladder portion 12 of the stent 10 includes a balloon 22, and the distal or renal portion 14 of the stent includes a balloon 24. The ends of the balloons 22, 24 are sealingly attached to the tubular member 20 such that the balloons can be inflated after implantation, preferably with a fluid, such as a liquid, semi-liquid, gel, or gas that contains a therapeutic agent. In a preferred embodiment, the balloons 22, 24 are filled with liquid saline containing a therapeutic agent. The balloons 22, 24 are illustrated in the inflated configuration in FIGS. 1-4. The balloon 22 serves to retain the proximal end of the stent 10 within the urinary bladder 30, while the balloon 24 serves to retain the distal end of the stent in the renal cavity 64. The balloons 22, 24 also act as reservoirs for fluids containing therapeutic agents that are directionally delivered by the stent 10 as described below.

In alternative embodiments, the stent 10 only includes one of the balloons 22, 24. Such an embodiment could also include one or more coiled retention end pieces, such as are described in U.S. Patent Application Publication US2003/0195456 A1, the entire disclosure of which is hereby incorporated by reference. Additionally, one embodiment of the stent 10 includes balloons 22, 24 and coils. For example, one or both of the ends of the stent 10 may also be coiled in a pigtail spiral or J-shape to further prevent the upward and/or downward migration of the stent in the lumen of the ureter due to, for example, day-to-day physical activity of the patient. A kidney end coil would help retain the stent within the renal pelvis and prevent stent migration down the ureter while a urinary bladder end coil positioned in the bladder would help prevent stent migration upward toward the kidney.

In a further embodiment, the stent 10 includes one or more additional balloons located between the proximal portion 12 and the distal portion 14 of the stent. For example, in one embodiment, the stent 10 includes a similarly configured medial balloon that elutes an agent for treating the ureter.

The balloons 22, 24 may be configured to inflate to any variety of desired shapes. Additionally, the balloons 22, 24 are preferably constructed from materials with similar properties to the tubular member 20, but should be compliant with a high percentage of elongation such as, for example, silicone or latex.

As is illustrated in FIG. 2, the tubular member 20 includes a first inflation lumen 26 and a second inflation lumen 28, which are used to inflate the balloons 22, 24 with a fluid containing a therapeutic agent. The lumens 26, 28 run along a portion of the length or along the entire length of the tubular member 20 and are separate from the drainage lumen 18. The first lumen 26 is in fluid communication with the proximal balloon 22 via an inflation port 30, which is an opening into the lumen 26 between the opposing, sealed ends of the balloon 22. The inflation port 30 allows fluid to pass from the lumen 26 into the balloon 22 so as to inflate the balloon. The lumen 26 also receives a one way check valve 32, such as a duck-bill or ball-type valve, that only permits fluid flow in the lumen 26 along the direction of inflation flow f1. The check valve 32 is located upstream of the inflation port 30 with respect to the direction of inflation flow f1 through the lumen 26. The lumen 26 also receives a filter 34, a metered orifice 36, and a plug 38, all of which are located successively downstream of the inflation port 30 with respect to the direction of inflation flow f1.

The portion of the lumen 26 located downstream of the port 30 with respect to the direction of flow f1 functions as a conduit for the delivery of the fluid containing the therapeutic agent after the stent 10 has been implanted and the balloon 22 has been inflated with the fluid. The metered orifice 36 is a flow control device that permits the elution of the fluid containing the therapeutic agent from the balloon 22 at the proximal portion 12 of the stent. In one embodiment, the metered orifice 36 is a glass tube having an outer diameter of approximately 0.020 inches and an inner, elongated flow channel 40 with a diameter of approximately 0.0005-0.010 inches, depending upon the desired rate of elution of the fluid containing the therapeutic agent. The filter 34 is a porous plug that helps prevent the metered orifice 36 from clogging.

As is illustrated in FIG. 2, the lumen 26 includes delivery port 42, which delivers the fluid containing the therapeutic agent from the lumen 26 and balloon 22 to an area exterior of and immediately adjacent proximal portion 12 of the stent 10. Hence, the port 42 is located upstream of the plug 38 with respect to the direction of elution flow f2 through the lumen 26. The plug 38 is a device that seals the lumen 26 at a location downstream of the port 42 with respect to the direction of elution flow f2. After the stent 10 is implanted, the balloon 22 is inflated by delivering the fluid containing the therapeutic agent to the lumen 26, through the valve 32, and through the port 30. Then, the fluid containing the therapeutic agent is delivered from the stent 10 at the proximal portion 12 when the fluid flows or eludes from the interior of the balloon 22 through the port 30, through the filter 34, through the metered orifice 36, and finally out of the port 42.

Figure 3:
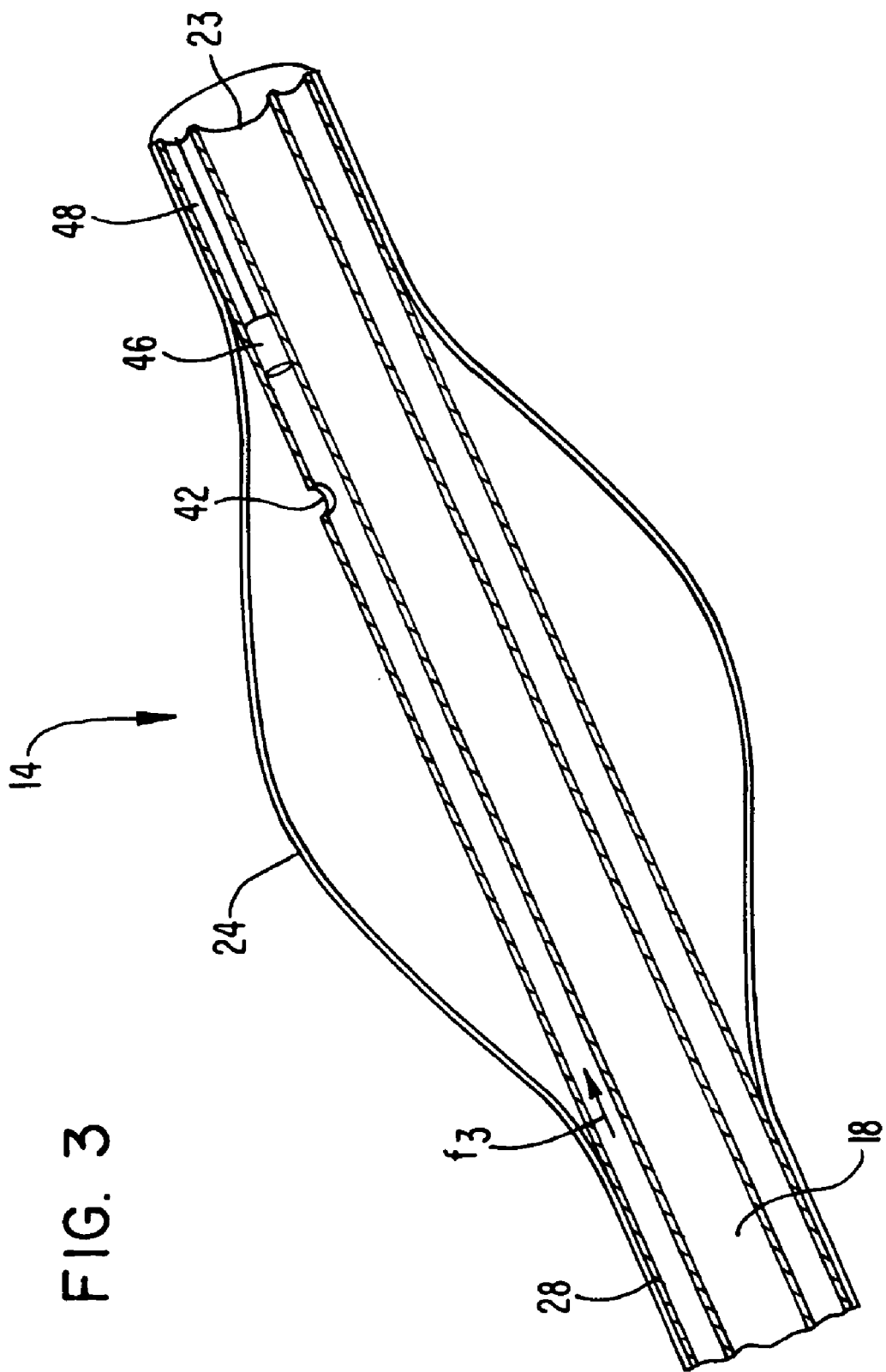
FIG. 3 is an enlarged detail view of the renal end of the ureteral stent illustrated in FIG. 1.

Referring to FIGS. 2 and 3, the second inflation lumen 28 is used to inflate the distal balloon 24 with a fluid containing a therapeutic agent. The lumen 28 runs the length of the tubular member 20 and is separate from the drainage lumen 18. The second lumen 28 is in fluid communication with the distal balloon 22 via an inflation port 42, which is an opening into the lumen 28 between the opposing, sealed ends of the balloon 24. The inflation port 42 allows fluid to pass from the lumen 28 into the balloon 24 so as to inflate the balloon. The lumen 28 also includes a one way check valve 44, such as a duck bill or ball type valve, that only permits fluid flow in the lumen 26 along the direction of inflation flow f3. The check valve 44 is located upstream of the inflation port 42 with respect to the direction of inflation flow f3 through the lumen 28. The lumen 28 also receives a filter 46 and a metered orifice 48, which are located successively downstream of the inflation port 42 with respect to the direction of inflation flow f3. The filter 46 and the metered orifice 48 may be identical to or different than the filter 34 and orifice 36 associated with the proximal balloon 22. For example, the orifice 48 may be configured to have a higher or lower fluid elution rate than that of the orifice 36.

The portion of the lumen 28 located downstream of the port 42 with respect to the direction of flow f3 functions as a conduit for the delivery of the fluid containing the therapeutic agent after the stent 10 has been implanted and the balloon 24 has been inflated with the fluid. The metered orifice 48 is a flow control device that permits the elution of the fluid containing the therapeutic agent from the balloon 24 at the distal portion 14 of the stent. In one embodiment, the metered orifice 48 is a glass tube having an outer diameter of approximately 0.020 inches and an inner, elongated flow channel 40 with a diameter of approximately 0.0005-0.010 inches, depending upon the desired rate of elution of the fluid containing the therapeutic agent. The filter 46 is a porous plug that helps prevent the metered orifice 48 from clogging.

As is illustrated in FIG. 3, the lumen 28 terminates at an opening at the distal end 23 of the tubular member 20. The distal opening of the lumen 28 functions as the delivery port for the fluid containing the therapeutic agent from the lumen 28 and balloon 24 to an area exterior of and immediately adjacent the distal portion 14 of the stent 10, i.e., such as the renal cavity. After the stent 10 is implanted, the balloon 24 is inflated by delivering the fluid containing the therapeutic agent to the lumen 28, through the valve 44, and through the port 42. Then, the fluid containing the therapeutic agent is delivered from the stent 10 at the distal portion 14 when the fluid flows or eludes from the interior of the balloon 24 back through the port 42, through the filter 46, through the metered orifice 48, and finally out of the distal opening of the lumen 28.

The balloons 22, 24 may be filled with identical or different fluids, such as gases, liquids, and mixtures of gases and liquids that contain one or more therapeutic agents. For example, therapeutic agents may be contained within a saline solution. Examples of classes of therapeutic agents include anesthetics, antipasmodic agents, anti-cholinergic agents, chemotherapeutic agents, or agents for transfection of genes. "Therapeutic agents" as used herein include genetic therapeutic agents, non-genetic therapeutic agents, and cells. Therapeutic agents may be used singly or in combination. Therapeutic agents may be, for example, nonionic or they may be anionic and/or cationic in nature. Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines, and (r) hormones.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

A wide range of therapeutic agent loadings can be used in connection with embodiments of the present invention, with the pharmaceutically effective amount being readily determined and ultimately depending, for example, upon the condition to be treated, the nature of the therapeutic agent itself, the tissue into which the dosage form is introduced, and so forth.

Examples of therapeutic agents or additives in addition to those listed above include those listed in the following classes.

Anti-inflammatory agents include steroidal and non-steroidal anti-inflammatory agents. Examples of non-steroidal anti-inflammatory drugs include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid and its derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids) include 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Non-narcotic analgesics include aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, flupro-quazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenyl-propylamine, tropenzile, trospium chloride, xenytropium bromide, and pharmaceutically acceptable salts thereof.

Antimicrobial agents include biocidal agents and biostatic agents as well as agents that possess both biocidal and biostatic properties, such as triclosan, chlorhexidine, nitrofurazone, benzalkonium chlorides, silver salts and antibiotics such as rifampin, gentamycin and minocyclin and combinations thereof.

Two anti-inflammatory and antispasmodic therapeutic agents for the practice of an embodiment of the present invention are (a) ketorolac and pharmaceutically acceptable salts thereof (e.g., the tromethamine salt thereof, sold under the commercial name Toradol®) and (b) 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial name Ditropan®).

The medical device of the present invention may also contain optional additives, including radio-opacifying agents, pigments, and other additives such as plasticizers and extrusion lubricants, within its structure.

The radio-opacifying agent facilitates viewing of the medical device during insertion of the device and at any point while the device is implanted. A radio-opacifying agent typically functions by scattering x-rays. The areas of the medical device that scatter the x-rays are detectable on a radiograph. Among radio-opacifying agents useful in the medical device of the present invention are included a bismuth salt such as bismuth subcarbonate, bismuth oxychloride, bismuth trioxide, barium sulfate, tungsten, and mixtures thereof, with bismuth salts typically being preferred.

Pigments include any biocompatible and pharmaceutically acceptable colorant, regardless of type or color, including titanium dioxide, phthalocyanine organic pigments, quinaridone organic pigments, carbon black, iron oxides, and ultramarines.

Figure 4:
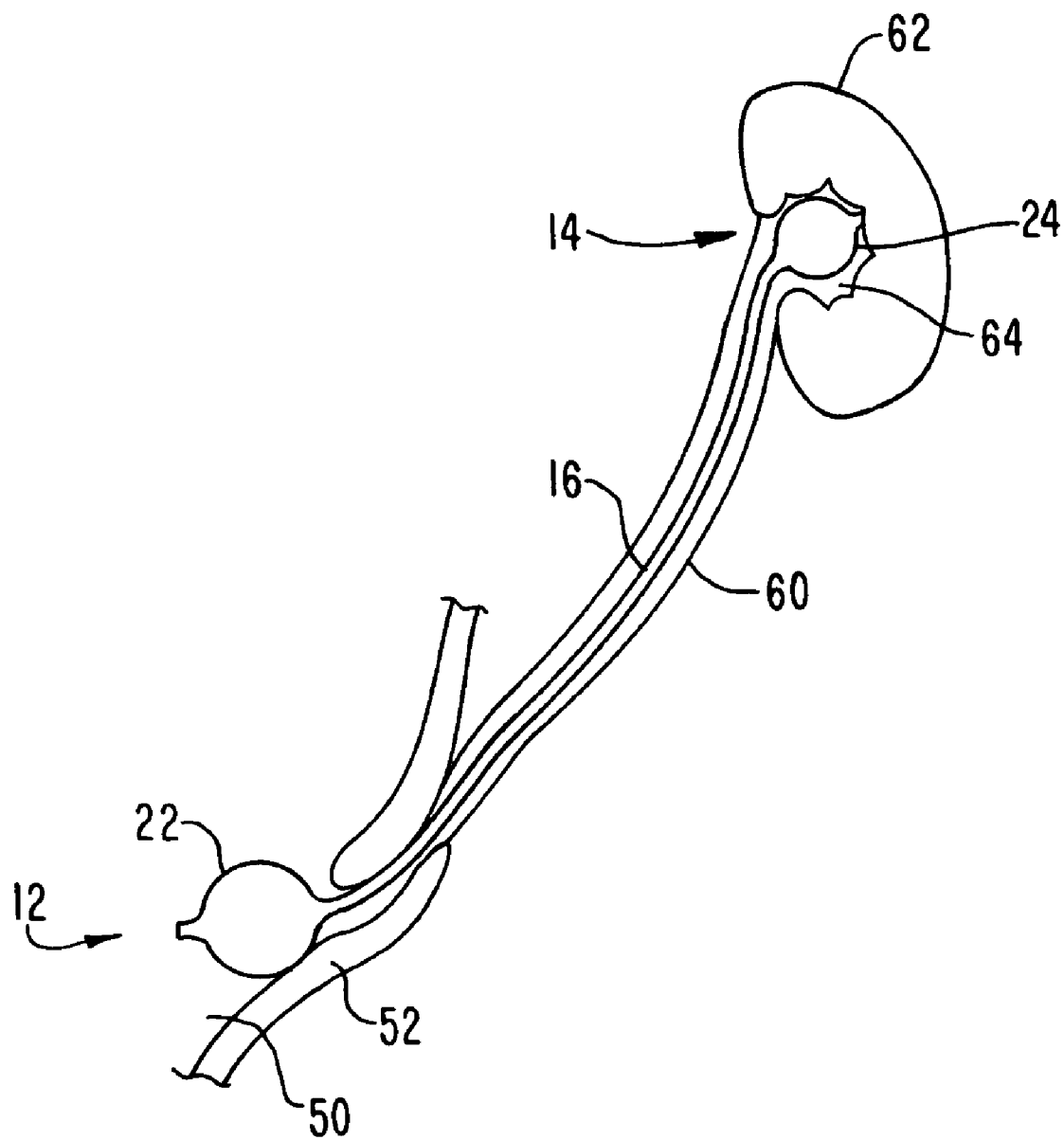
FIG. 4 is plan view of the ureteral stent illustrated in FIG. 1 in a clinical application according to one embodiment of the invention.

Referring now to FIG. 4, a clinical application of ureteral stent 10 according to the invention is depicted. The ureteral stent 10 may be introduced to the body either percutaneously in an antigrade fashion, using for example, an adaptation of the Seldinger technique, or cystoscopically in a retrograde fashion. Hence, in one embodiment of the invention, a pusher tube (not shown) is used to deliver the stent 10 through a cytoscope over a guide wire (not shown) and into the ureter 60. In another embodiment, stent 10 is introduced endoscopically without the use of pusher tube. Before stent 10 is inserted into the body, the deflated balloons 22, 24 are substantially the same diameter in the deflated form as the proximal and distal portions 12, 14 of the stent 10. After insertion into the body, the balloon 22 is inflated with the fluid containing the therapeutic agent to a suitable diameter, such as 3 to 10 mm, preferably 5 mm for retention of the proximal portion 12 of the stent 10 within the urinary bladder 50 and for delivery of the fluid containing the therapeutic agent to the urinary bladder. After insertion into the body, the balloon 24 is also inflated with the fluid containing the therapeutic agent to a suitable diameter, such as 3 to 10 mm, for retention of the distal portion 12 of the stent 10 within the renal pelvis or cavity 64 of the kidney 62 and for delivery of the fluid containing the therapeutic agent to the renal cavity 64, as best seen in FIG. 4.

Referring again to FIG. 4, once inflated, the balloon 22 is positioned proximal to the bladder wall 52 thereby minimizing migration of stent 10 within the ureter 50 and maintaining the elongated body portion 16 in situ. The balloon 24 is positioned proximal to the wall of the renal cavity 64 thereby minimizing migration of stent 10 within the kidney 62 and maintaining the elongated body portion 16 in situ. To remove the stent 10, the balloons 22, 24 are deflated via end-effector valves or other devices (not illustrated). Additionally, the balloons 22, 24 can be deflated by piercing the check valves 32, 44 or by directly piercing and aspirating the balloons.

Figure 5:
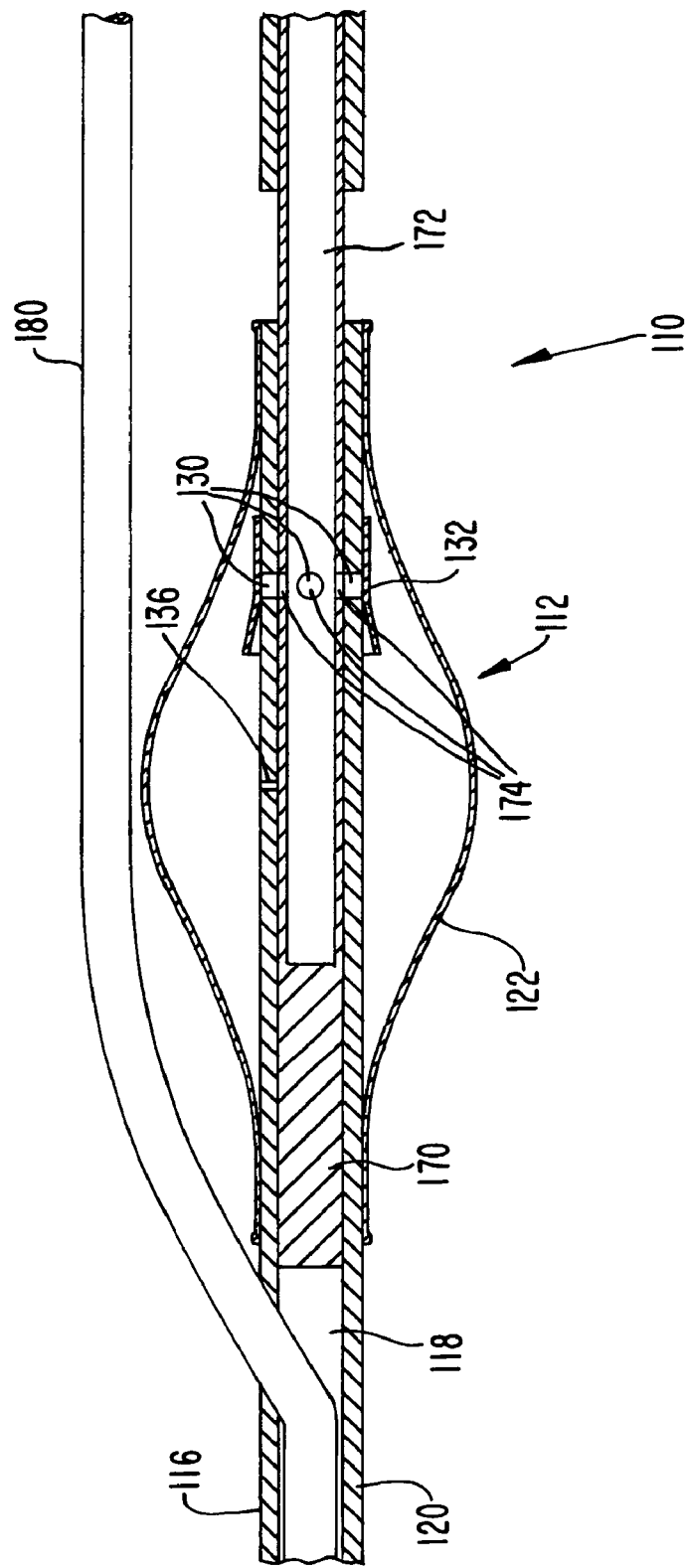
FIG. 5 is a partial cross-sectional view of a ureteral stent according to another embodiment of the invention.

FIG. 5 illustrates a ureteral stent 110 in accordance with an alternative embodiment of the invention. Like the stent 10, the stent 110 is a drainage device that, when positioned within the ureter of a mammal, assists in reducing fluid retention by facilitating the drainage of urine from the kidney through the ureter and into the urinary bladder. The stent 110 may be used in the same manner as the stent 10 described above and the foregoing discussion of the benefits and functions of the stent 10 also applies to the stent 110. Thus, the stent 110 illustrated in FIG. 5 has been assigned corresponding reference numbers as the stent 10, increased by one hundred. The stent 110 illustrated in FIG. 5 also include additional features and inherent functions, as described further below.

The stent 110 is configured for implantation within the ureter of a patient, and includes a proximal or bladder portion 120, a distal or renal portion (not illustrated), and an elongated body portion 116 between the proximal and distal portions. The stent 110 includes a drainage lumen 118 that extends the length of the stent to facilitate the drainage of urine from the kidney through the ureter and into the urinary bladder. The ureteral stent 110 is tubular in shape, terminating in two opposing ends: a kidney distal end and a urinary bladder proximal end.

As is illustrated in FIG. 5, the stent 110 includes a tubular member 120 that extends from the proximal portion to the distal portion and that defines the drainage lumen 118. The proximal or bladder portion 112 of the stent 110 includes a balloon 122. The distal or renal portion of the stent may include a balloon identical to the balloon 122. Alternatively, the distal or renal portion of the stent 110 may include one or more coiled retention end pieces, as described above.

The ends of the balloon 122 are sealingly attached to the tubular member 120 such that the balloons can be inflated after implantation, preferably with the fluid containing the therapeutic agent. The balloon 122 is illustrated in the process of being inflated in FIG. 5. The balloon 122 serves to retain the proximal end of the stent 110 within the urinary bladder, and may be configured to inflate to any variety of desired shapes.

As is illustrated in FIG. 5, the tubular member 120 includes a plurality of ports 130 that are used to inflate the balloon 122 with the fluid containing the therapeutic agent. Hence, the lumen 118 is in fluid communication with the balloon 122 via the ports 130, which are openings into the lumen 118 between the opposing, sealed ends of the balloon 122. The ports 130 allow fluid to pass from the lumen 126 into the balloon 122 so as to inflate the balloon. As is illustrated in FIG. 5, the stent 110 also includes a one way check valve 132, which is in the form of a flap over the ports 130. In alternative embodiments, the check valve 132 may be duck-bill or ball-type valve located in the ports 130 that only permit fluid flow into the balloon, not out of the balloon.

The tubular member also includes a metered orifice 136, which is a flow control device that permits the elution of the fluids containing therapeutic agent from the balloon 122. In the illustrated embodiment, the metered orifice 136 is a slit or small port in the wall of the tubular member 120. The orifice 136 communicates the interior of the inflated balloon with the interior of the lumen 118 such that fluid can elute from the balloon into the lumen 118 after the stent has been implanted. The stent 110 can also include a filter (not shown) to prevent the metered orifice 136 from clogging.

FIG. 5 illustrates the balloon 122 being inflated with a fluid containing a therapeutic agent. A pushrod 170 is inserted into the stent 110. The pushrod 170 has a lumen 172 and openings 174. When the push rod is fully inserted into the stent 110, the openings 174 are aligned with the ports 130 such that the fluid containing a therapeutic agent can be delivered through the lumen 172, through the openings 174, through the ports 130, and into the balloon 122. After the balloon 122 is inflated, the pushrod 170 is removed. FIG. 5 also illustrates a guidewire 180 being used to guide the stent 110 during implantation. The stent 110 is positioned in the bladder and is passed into the ureter. The guidewire 180 is of sufficient stiffness and maneuverability and is inserted into the ureter under endoscopic guidance. When access past the ureteral obstruction of the kidney is achieved, for example, the stent is introduced to the ureter over the wire by the pushrod 170 acting on the trailing or proximal edge of the stent. The guidewire and stent are positioned with imaging guidance, such as a direct vision scope or fluoroscopy. Once the stent is implanted, the push rod is disengaged from the distal end of the stent with a pusher, and the push rod is removed. The balloon 122 is positioned proximal to the bladder wall thereby minimizing migration of stent 110 within the ureter and maintaining the elongated body portion 116 in situ. Additionally, the fluid containing a therapeutic agent is delivered from the stent 110 at the proximal portion 112 when the fluid flows or eludes from the interior of the balloon 122 through the metered orifice 136 through the lumen 118, and finally out the proximal end of the tubular member.

As will be appreciated, embodiments of stents and catheters according to the present invention may be used in areas of the body other than in the ureter, such as in the urethra and gall bladder. Additionally, the therapeutic agent may vary depending upon the specific application.

In alternative embodiments of the ureteral stent 10, the previously described balloons 22, 24, 122 may not function to retain the stent in place. For example, the stent may include other retention devices such that the balloons primarily function as reservoirs for fluid containing a therapeutic agent. Additionally, the balloons 22, 24, 122 and/or the tubular member 20 may include valves to permit the bleeding of gases when the balloons are being inflated.

Figure 6:
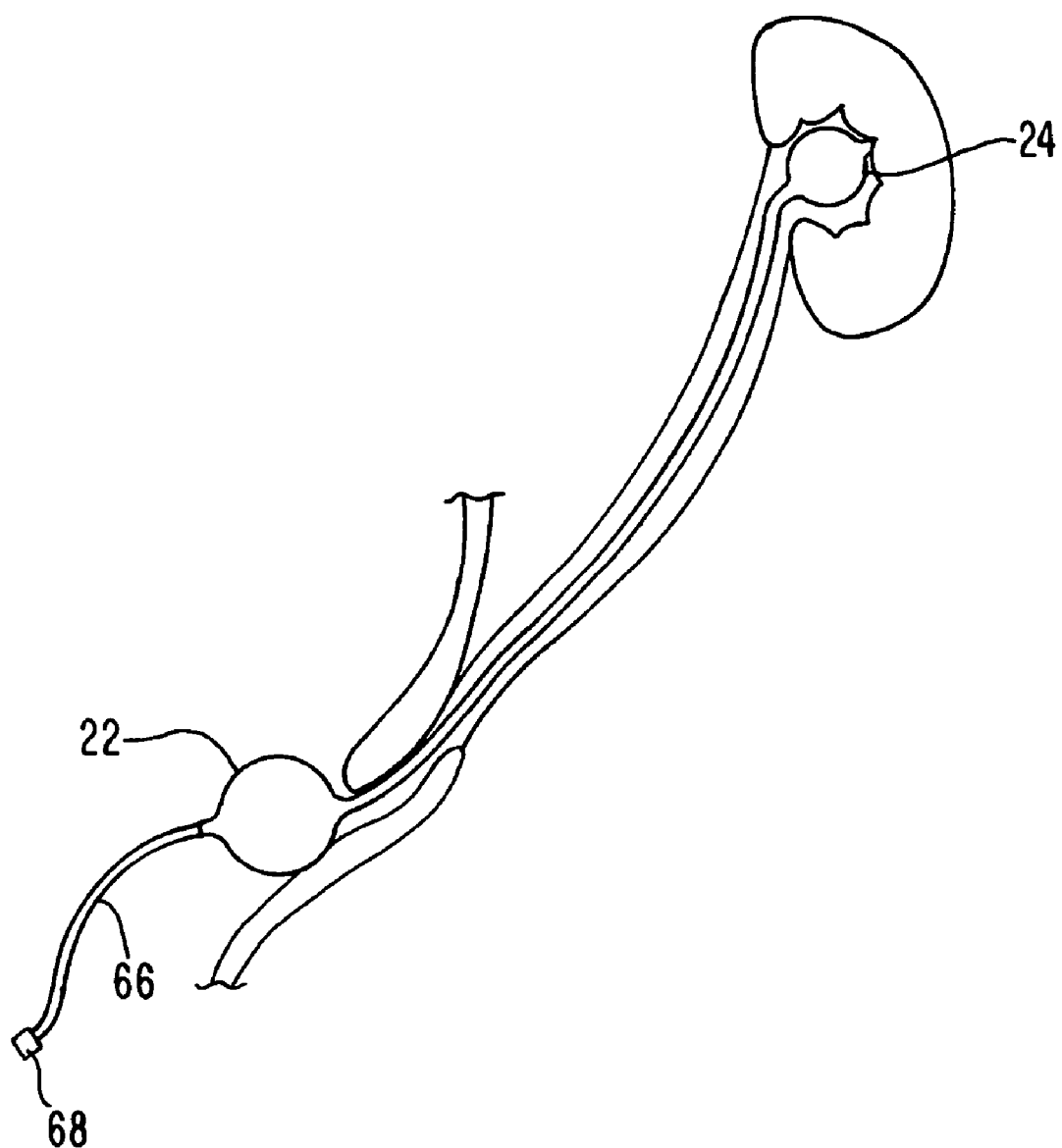
FIG. 6 is plan view of a ureteral catheter according to one embodiment of the invention, where the ureteral catheter includes the stent illustrated in FIG. 1 and is illustrated in a clinical application.

In accordance with another embodiment of the invention, the ureteral stent 10 defines part of a ureteral catheter. For example, as is illustrated in FIG. 6, the stent 10 is attached to and in fluid communication with a ureteral access tube 66 that protrudes from the body of the patient. The access tube 66 has a hub 68 and internal lumens that are in fluid communication with the lumens 26, 28 such that a user can repeatedly inflate and/or drain the balloons 22, 24 as desired. In one embodiment, the hub 68 has multiple luers for communication with the lumens of the tube 66 and for draining the balloons 22, 24. Hence, a portion of the access tube 66 and the hub 68 remain outside the body of the patient through the urethra. This advantageously provides the physician with the option to refill the balloons 22, 24 at periodic time intervals to provide a longer therapeutic duration. In accordance with another embodiment, the stent 10 defines part of a nephrostomy catheter. In this embodiment, the stent 10 is attached to and in fluid communication with a nephrostomy access tube that protrudes from the body of the patient. The nephrostomy access tube also has a hub and internal lumens that are in fluid communication with the lumens 26, 28 such that a user can repeatedly inflate and/or drain the balloons 22, 24 as desired. Hence, a portion of the nephrostomy access tube and the hub remain outside the body of the patient through a percutaneous incision.

The principles, preferred embodiments, and modes of operation of the present invention have been described in the foregoing description. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes, and equivalents which fall within the spirit and scope of the present invention.

What is claimed is:

1. A device for placement within a body of a patient, comprising:
   an elongated member having a first end portion and a second end portion, the elongated member defining a first lumen and a second lumen, the first lumen extending from the first end portion to the second end portion;
   an inflatable member coupled to the elongated member between the first end portion of the elongated member and the second end portion of the elongated member, the second lumen being in fluid communication with an interior of the inflatable member, the inflatable member being configured to be inflated with a fluid conveyed to the inflatable member via the second lumen and being configured to deliver the fluid to the body of the patient when the device is placed within the body; and
   a valve disposed within the second lumen to permit fluid to flow through the second lumen towards the inflatable member but to inhibit flow of fluid away from the inflatable member.

2. The device of claim 1, wherein the elongated member defines a first opening fluidically coupling the second lumen with the interior of the inflatable member and a second opening fluidically coupling the second lumen with an exterior of the elongated member.

3. The device of claim 1, wherein the elongated member defines a first opening fluidically coupling the second lumen with the interior of the inflatable member, a second opening fluidically coupling the second lumen with an exterior of the elongated member, and a third opening fluidically coupling the second lumen with the exterior of the elongated member, the first opening disposed between a first end portion of the inflatable member and a second end portion of the inflatable member, the second opening being disposed between the inflatable member and the first end portion of the elongated member, the third opening being disposed between the inflatable member and the second end portion of the elongated member.

4. The device of claim 1, wherein the inflatable member has a first end portion coupled to the elongated member and a second end portion coupled to the elongate member.

5. The device of claim 1, wherein the fluid includes a therapeutic agent.

6. The device of claim 1, wherein the device is a ureteral stent and the first lumen is configured to convey urine from a kidney of the patient to a bladder of the patient.

7. The device of claim 1, wherein the inflatable member is configured to help retain the device within the body of the patient.

8. The device of claim 1, wherein the first end portion of the elongated member is configured to be placed in a bladder of the patient and the second end portion of the elongated member is configured to be placed in a kidney of the patient.

9. The device of claim 1, wherein the first end portion of the elongated member is configured to be placed within a bladder of the patient.

10. The device of claim 1, the inflatable member being a first inflatable member, the fluid being a first fluid, the device further comprising:
    a second inflatable member coupled to the elongated member between the first end portion of the elongated member and the second end portion of the elongated member, the second inflatable member being configured to be inflated with a second fluid and being configured to deliver the second fluid to the body of the patient when the device is placed within the body.

11. The device of claim 10, wherein the elongated member defines a third lumen, the third lumen being in fluid communication with an interior of the second inflatable member.

12. The device of claim 11, wherein a first metered orifice is disposed within the second lumen and a second metered orifice is disposed within the third lumen.

13. The device of claim 11, wherein the first inflatable member is configured to be placed in a bladder of the patient, the second inflatable member is configured to be placed in a kidney of a patient.

14. The device of claim 11, wherein the first inflatable member is configured to help retain the device within the body of the patient.

15. The device of claim 1, further comprising:
    a metered orifice being disposed within the second lumen.

16. A device for placement within a body of a patient, comprising:
    an elongated member having a first end portion and a second end portion, the elongated member including a sidewall, a valve, and defining a lumen; and
    an inflatable member coupled to the elongated member between the first end portion of the elongated member and the second end portion of the elongated member, the sidewall of the elongated member defining an opening and an orifice, the orifice being configured to fluidically couple an interior of the inflatable member to the lumen, the valve being configured to communicate fluid from the lumen to the inflatable member, the inflatable member being configured to be inflated with a fluid and being configured to deliver the fluid to the body of the patient when the device is placed within the body.

17. The device of claim 16, wherein the first end portion of the elongated member is configured to be placed in a kidney of the patient and the lumen is configured to convey urine from the kidney of the patient.

18. The device of claim 16, wherein the inflatable member is configured to help retain the device within the patient.

19. The device of claim 16, further comprising:

an insertion member having a sidewall and defining an internal lumen, the sidewall of the insertion member defining an opening, the opening defined by the sidewall of the insertion member being configured to be aligned with the opening defined by the elongated member to convey fluid from the internal lumen of the insertion member to the inflatable member.

20. The device of claim 16, wherein the first end portion of the elongated member is configured to be placed within a kidney of the patient, the second end portion of the elongated member is configured to be placed within a bladder of a patient.

21. A method of placing a device into a body of a patient, comprising:

inserting a first end portion of the device into a kidney of the patient, the device having an elongated member, a first inflatable member coupled to the elongated member, and a second inflatable member coupled to the elongated member;

inflating the first inflatable member with a first fluid via a first lumen defined by the elongated member; and inflating the second inflatable member with a second fluid via a second lumen defined by the elongated member.

22. A method of placing a device into a body of a patient, comprising:

inserting a first end portion of the device into a bladder of the patient; the device having an elongated member, a first inflatable member coupled to the elongated member, and a second inflatable member coupled to the elongated member;

inflating the first inflatable member with a first fluid via a first lumen defined by the elongated member; and inflating the second inflatable member with a second fluid via a second lumen defined by the elongated member.

23. The method of claim 22, wherein the inserting includes placing the first inflatable member in the kidney of the patient and placing the second inflatable member in a bladder of the patient, the first inflatable member being coupled to the first end portion.

24. The method of claim 21, further comprising:

inserting a second end portion of the device into a kidney of the patient, the second inflatable member being coupled to the second end portion.

25. A device for placement within a body of a patient, comprising:

an elongated member having a first end portion and a second end portion, the elongated member defining a first lumen and a second lumen, the first lumen extending from the first end portion to the second end portion;

an inflatable member coupled to the elongated member between the first end portion of the elongated member and the second end portion of the elongated member, the second lumen being in fluid communication with an interior of the inflatable member, the inflatable member being configured to be inflated with a fluid conveyed to the inflatable member via the second lumen and being configured to deliver the fluid to the body of the patient when the device is placed within the body; and a metered orifice being disposed within the second lumen.

26. The device of claim 25, wherein the elongated member defines a first opening fluidically coupling the second lumen with the interior of the inflatable member and a second opening fluidically coupling the second lumen with an exterior of the elongated member.

27. The device of claim 25, the inflatable member being a first inflatable member, the fluid being a first fluid, the device further comprising:

a second inflatable member coupled to the elongated member between the first end portion of the elongated member and the second end portion of the elongated member, the second inflatable member being configured to be inflated with a second fluid and being configured to deliver the second fluid to the body of the patient when the device is placed within the body.

28. The device of claim 27, wherein the elongated member defines a third lumen, the third lumen being in fluid communication with an interior of the second inflatable member.

29. The device of claim 25, further comprising:

a valve disposed within the second lumen.

* * * * *